(12) United States Patent
Hu et al.

(10) Patent No.: US 6,444,838 B2
(45) Date of Patent: Sep. 3, 2002

(54) PROCESS FOR THE PREPARATION OF 1,4-DIARYL-2-FLUORO-4-CYANO-2-BUTENES AND INTERMEDIATES USEFUL THEREFOR

(75) Inventors: Yulin Hu, Plainsboro, NJ (US); David Allen Hunt, Clifton Park, NY (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/849,298

(22) Filed: May 4, 2001

Related U.S. Application Data

(60) Provisional application No. 60/201,826, filed on May 4, 2000.

(51) Int. Cl.⁷ .............................................. C07C 253/14
(52) U.S. Cl. ...................................... 558/342; 558/410
(58) Field of Search .................................. 558/342, 410

(56) References Cited

U.S. PATENT DOCUMENTS

| | | |
|---|---|---|
| 5,248,834 A | 9/1993 | Elliott et al. |
| 5,849,958 A * | 12/1998 | Barnes et al. ............... 568/634 |
| 5,998,673 A | 12/1999 | Barnes et al. |
| 6,235,754 B1 * | 5/2001 | Watson et al. ............... 514/315 |

FOREIGN PATENT DOCUMENTS

| | | | |
|---|---|---|---|
| EP | 0811593 | * | 10/1997 |
| GB | 2288 803 A | | 11/1995 |
| WO | WO 94/06741 | | 3/1994 |
| WO | WO 97/16067 | | 5/1997 |

* cited by examiner

*Primary Examiner*—Robert W. Ramsuer
*Assistant Examiner*—Golam M. M. Shameem
(74) *Attorney, Agent, or Firm*—Keil & Weinkauf

(57) ABSTRACT

The present invention provides a process for the preparation of pesticidal 1,4-diaryl-2-fluoro-4-cyano-2-butene compounds having the structural formula I

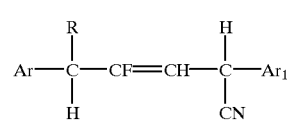

and intermediates useful therefor.

11 Claims, No Drawings

PROCESS FOR THE PREPARATION OF 1,4-DIARYL-2-FLUORO-4-CYANO-2-BUTENES AND INTERMEDIATES USEFUL THEREFOR

This application claims priority from copending provisional application(s) Ser. No. 60/201,826 filed on May 4, 2000.

BACKGROUND OF THE INVENTION

Certain fluoroolefin compounds are known to possess insecticidal and acaricidal activity (see, e.g., U.S. Pat. No. 5,248,834; GB 2,288,803-A; WO 94/06741; WO 97/16067; and U.S. Pat. No. 5,998,673. However, the fluoroolefin compounds disclosed in those patents and patent applications are outside the scope of the present invention. U.S. Pat. No. 5,248,834 generically discloses certain 1-aryl-1-(3-aryl-1,2-difluoroprop-1-enyl)cyclopropane compounds. However, that patent does not provide a method to prepare those compounds. In fact, U.S. Pat. No. 5,248,834 does not provide a method to prepare any fluoroolefin compounds.

1,4-diaryl-2-fluoro-4-cyano-2-butenes and a method for their preparation are described in U.S. Pat. No. 5,998,673. Said compounds are useful as insecticidal and acaricidal agents and for protecting plants from damage caused by insect and acarid attack and infestation. Although a method for the preparation of said agents is known, alternative more effective methods contribute to the enhanced availability of these useful insecticidal and acaricidal agents.

It is, therefore, an object of the present invention to provide a process for the preparation of 1,4-diaryl-2-fluoro-4-cyano-2-butenes.

It is also an object of the present invention to provide intermediates useful in said process.

These and other objects of the present invention will become more apparent from the detailed description thereof set forth below.

SUMMARY OF THE INVENTION

The present invention provides a process for the preparation of insecticidal and acaricidal 1,4-diaryl-2-fluoro-4-cyano-2-butene compounds of structural formula I

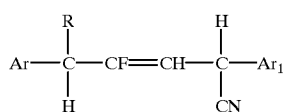

wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is hydrogen, $C_1$–$C_4$alkyl, $C_1$–$C_4$haloalkyl, $C_3$–$C_6$cycloalkyl or $C_3$–$C_6$halocycloalkyl; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; or the optical isomers thereof; or
the cis and trans isomers thereof
which process comprises the following steps:

(a) reacting an intermediate of formula II

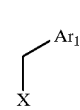

wherein $Ar_1$ is defined as above and X is a nucleophilic replaceabale leaving group, such as halogen, alkylsulphonyloxy or arylsulphonyloxy, especially chloro, bromo, iodo, tosyloxy, mesyloxy or the like, with a cyanide delivering reagent in a first solvent to afford a cyano intermediate of formula III;

(b) reacting said cyano intermediate III with an aldehyde of formula IV

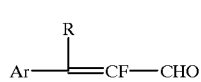

in the presence of a base in a second solvent to yield an anion which is acidified to afford a diene of formula V

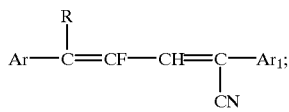

and (c) reacting said diene V with magnesium in the presence of a third solvent.

This invention also provides intermediate dienes of structural formula V.

DETAILED DESCRIPTION OF THE INVENTION

Although a method for the preparation of insecticidal and acaricidal 1,4-diaryl-2-fluoro-4-cyano-2-butenes is described in U.S. Pat. No. 5,998,673, alternative more effective methods contribute to the enhanced availability of these useful insecticidal and acaricidal agents.

Advantageously, the present invention provides an effective and practical method for the preparation of 1,4-diaryl-2-fluoro-4-cyano-2-butenes of formula I,

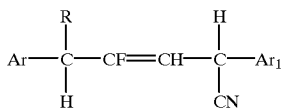

wherein Ar, $Ar_1$ and R are defined as above.

In accordance with the process of the invention intermediate II is treated with a cyanide delivering reagent in a polar aprotic solvent (first solvent) to afford the cyano intermediate III. Cyano intermediate III is reacted with an aldehyde of formula IV in the presence of a base optionally in the presence of a second solvent to yield an intermediate which is acidified to afford a diene of formula V; and said diene V is reacted with magnesium in the presence of a protic solvent (third solvent) to provide 1,4-diaryl-2-fluoro-4-cyano-2-butene I. The process is depicted in Flow Diagram I.

Flow Diagram I

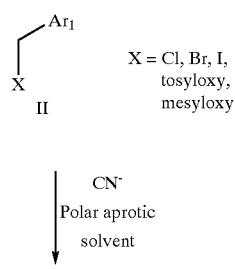

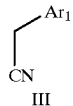

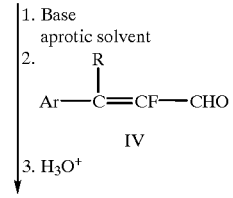

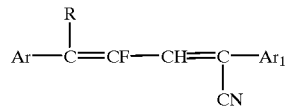

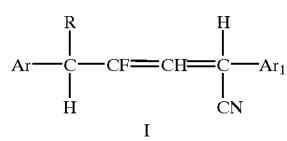

Intermediate aldehydes IV may be prepared as described in U.S. Pat. No. 5,998,673.

First solvents suitable for use in the inventive process include polar aprotic solvents such as dimethylformamide, dimethylsulfoxide, N-methylpyrrolidone or the like, preferably dimethylsulfoxide.

Second solvents suitable for use in the inventive process include aprotic solvents such as tetrahydrofuran, diethyl ether and the like, preferably tetrahydrofuran.

Third solvents suitable for use in the inventive process include protic solvents such as alkanols, preferably methanol or ethanol.

Cyanide ion delivering reagents include alkali metal cyanides and quarternary ammonium cyanides, preferably sodium cyanide or potassium cyanide.

Bases suitable for use in the inventive process are alkali metal amides, such as lithium amide, lithium dimethylamide, lithium diisopropylamide, sodium bis(trimethylsilyl)amide, magnesiochlorodiethylamide ($Et_2NMgCl$), or the like, preferably lithium diisopropylamide.

Bases may be present in amounts ranging from catalytic to excess amounts such as 10 mole % to 4.0 molar excess.

Acids suitable for use in the process of the invention include strong mineral acids such as HCl, HBr or $H_2SO_4$, preferably HCl or $H_2SO_4$.

In actual practice, intermediate II, preferably wherein X is Br, is treated with at least one molar equivalent of a cyanide delivering reagent, preferably sodium cyanide, in a polar aprotic solvent, preferably dimethyl sulfoxide, to yield the cyano intermediate III; said cyano intermediate III is treated with aldehyde IV in the presence of a base, preferable an alkali metal amide, preferably lithium diisopropylamide in an aprotic solvent, preferably tetrahydrofuran, to yield an intermediate which on acidification, preferably with hydrochloric acid, affords diene (V); said diene (V) is reacted with magnesium in the presence of a protic solvent preferably an alkanol, preferably methanol, or ethanol, to provide the desired 1,4-diaryl-2-fluoro-4-cyano-2-butene I.

The process depicted in Flow Diagram I provides 1,4-diaryl-2-fluoro-4-cyano-2-butene I having predominantly the (Z)-configuration. Formula I compounds wherein the double bond is in the (E)—configuration may be prepared by isomerizing 1,4-diaryl-2-fluoro-4-cyano-2-butene I which are predominantly in the (Z)—configuration using conventional procedures such as exposure to light.

In formula I above, 5-and 6-membered heteroaromatic rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formula I above.

Exemplary of halogen hereinabove are fluorine, chlorine, bromine and iodine. The terms "$C_1$–$C_4$haloalkyl", "$C_3$–$C_6$halocycloalkyl" and "$C_1$–$C_4$haloalkoxy" are defined as a $C_1$–$C_4$alkyl group, a $C_3$–$C_6$cycloalkyl group and a $C_1$–$C_4$alkoxy group substituted with one or more halogen atoms, respectively.

The present invention also provides compounds of formula V wherein the variables have the meanings as defined in formula I.

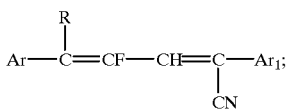

V

In compounds of formulae I and V respective following meanings for groups R are preferred: R is $C_1$–$C_4$alkyl; or $C_3$–$C_6$cycloalkyl especially isopropyl or cyclopropyl.

Compounds of formulae I and V, resp. are [referred. Wjereom Ar denotes phenyl which is substituted by halogen or $C_1$–$C_4$alkoxy.

Preference also is given to compounds of formulae I and V, resp. wherein $Ar_1$ is 3-phenoxyphenyl unsubstituted or substituted with any combination of from one to six halogen, $C_1$–$C_4$alkyl, $C_1$–$C_4$haloalkyl, $C_1$–$C_4$alkoxy, or $C_1$–$C_4$haloalkoxy, 3-biphenyl unsubstituted or substituted with any combination of from one to five halogen, $C_1$–$C_4$alkyl, $C_1$–$C_4$haloalkyl, $C1$–$C_4$alkoxy or $C_1$–$C_4$haloalkoxy.

Moreover, particular preference is given to compounds wherein $Ar_1$ is 3-phenoxyphenyl unsubstituted or substituted with any combination of from one to six halogen, $C_1$–$C_4$alkyl, $C_1$–$C_4$haloalkyl, $C_1$–$C_4$alkoxy or $C_1$–$C_4$haloalkoxy, particularly 3-phenoxy-4-halogen-phenyl, 3-(4'-halogen-phenoxy)-phenyl or 3-(4'-halogen-phenoxy)-4-halogen-phenyl.

Compounds of formulae I and V, resp. are especially preferred
wherein
Ar is phenyl optionally substituted with any combination of from one to three halogen, $C_1$–$C_4$alkyl, $C_1$–$C_4$haloalkyl, $C1$–$C_4$alkoxy or $C_1$–$C_4$haloalkoxy groups;

R is hydrogen, $C_1$–$C_4$alkyl, $C_1$–$C_4$haloalkyl, $C_3$–$C_6$cycloalkyl or $C_3$–$C_6$halocycloalkyl;
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

Preferred compounds of the invention are those compounds of formula V wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is hydrogen, $C_1$–$C_4$alkyl, $C_1$–$C_4$haloalkyl, $C_3$–$C_6$cycloalkyl or $C_3$–$C_6$halocycloalkyl;
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or
3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred compounds of the invention are those compounds of formula V wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is isopropyl or cyclopropyl; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Particularly preferred compounds of the invention are those formula V compounds wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R is cyclopropyl; and
$Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Moreover, particular preference is given to compounds of formula I' and V', resp. wherein the variables have the meanings given in table A:

TABLE A (I')

(V')

| No. | Z | R | Y | W |
|---|---|---|---|---|
| A-1 | Cl | cyclopropyl | H | H |
| A-2 | Cl | CH(CH₃)₂ | F | H |
| A-3 | Cl | CH(CH₃)₂ | H | H |
| A-4 | OCH₂CH₃ | CH(CH₃)₂ | F | H |
| A-5 | OCH₂CH₃ | CH(CH₃)₂ | F | H |
| A-6 | OCH₂CH₃ | cyclopropyl | H | H |
| A-7 | OCH₂CH₃ | CH(CH₃)₂ | H | F |
| A-8 | Cl | CH(CH₃)₂ | H | F |
| A-9 | F | cyclopropyl | F | H |
| A-10 | OCH₂CH₃ | cyclopropyl | H | H |
| A-11 | F | cyclopropyl | H | H |

With due modification of the starting compounds, the protocols shown in the synthesis examples below were used for obtaining further compounds I and V.

EXAMPLE 1

Preparation of (4-Fluoro-3-phenoxyphenyl) acetonitrile

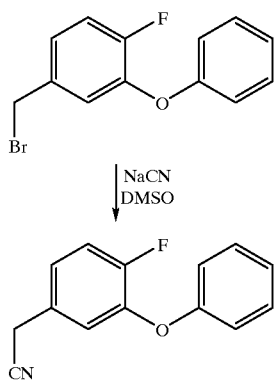

A mixture of α-bromo-4-fluoro-3-phenoxytoluene (2.65 g, 0.0094 mol) and sodium cyanide (0.735 g, 0.0141 mol) in dimethyl sulfoxide (15 ml) was heated at 50° C. for 35 min and 90° C. for 35 min. The cooled reaction mixture was diluted with water and extracted with ethyl acetate. The combined organic extracts were washed with water, saturated brine, dried over anhydrous sodium sulfate, and concentrated in vacuo to an off-white oil (1.8 g, 85.7%) which is characterized by IR, ¹HNMR, ¹³CNMR and ¹⁹FNMR analyses.

EXAMPLE 2

Preparation of 1-(p-Chlorophenyl)-1-cyclopropyl-2-fluoro-4-(4-fluoro-3-phenoxyphenyl)-4-cyano-1, 3-butadiene

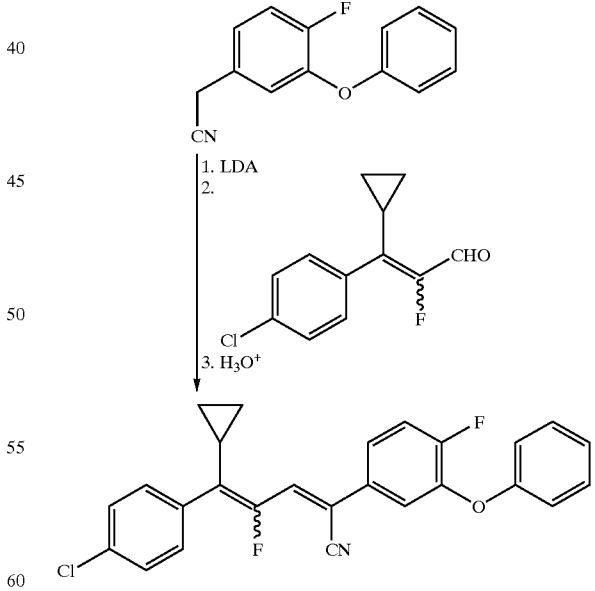

To a stirred solution of (4-fluoro-3-phenoxyphenyl)-acetonitrile (447.2 mg, 2.1 mmol) in anhydrous tetrahydrofuran (5 ml) under nitrogen at −78° C. is added via syringe a solution of lithium diisopropylamide in tetrahydrofuran (1.16 ml of 0.20M, 2.31 mmol). The reaction mixture is allowed to warm to room temperature and then stirred for 2 hr. The stirred reaction mixture is then cooled to −78° C. and a solution of p-chloro-β-cyclopropyl-α-fluorocinnamaldehyde (449.3 mg, 2 mmol) in tetrahydrofuran (2 ml) is added via syringe. The reaction mixture is allowed to warm to room temperature and stirred for 48 hr. The reaction mixture is diluted with ethyl acetate and 2N hydrochloric acid, and the layers separated. The aqueous layer is extracted with ethyl acetate, and the combined organic layers washed with 2N hydrochloric acid, water, dried over anhydrous sodium sulfate and concentrated in vacuo to a brown residue. Flash chromatography of this residue on silica gel eluting with ethyl acetate/hexane (⅙) afforded the title compound as a syrup (500 mg, 55.3%), which solidified on trituration with ether to yield a pale yellow solid (mp 110–112° C.) which is characterized by $^1$HNMR, $^{13}$CNMR, $^{19}$FNMR, IR and mass spectral analyses.

EXAMPLE 3

Preparation of 1-[1-(p-Chlorophenyl)-2-fluoro-4-(4-fluoro-3-phenoxyphenyl)-4-cyano-2-butenyl]-cyclopropane, (R, S)-(Z)-

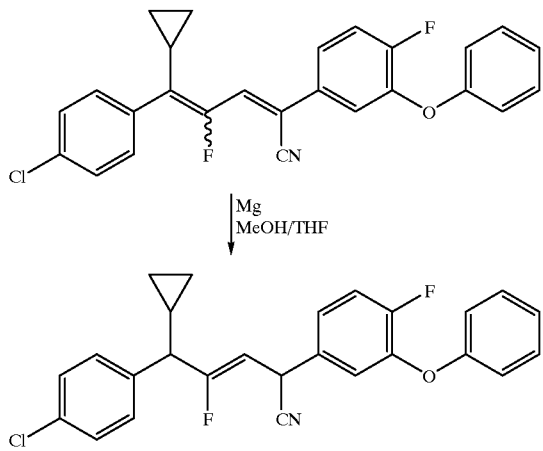

A mixture of 1-(p-chlorophenyl)-1-cyclopropyl-2-fluoro-4-(4-fluoro-3-phenoxyphenyl)-4-cyano-1,3-butadiene (335 mg, 0.77 mmol) and magnesium (93.8 mg, 3.86 mmol) in methanol (3 ml) and anhydrous THF (2 ml) is refluxed under nitrogen for 3 hr. The cooled reaction mixture is acidified with 2N hydrochloric and extracted with ethyl acetate. The combined extracts are washed with 2N hydrochloric acid, water, dried over anhydrous sodium sulfate, and concentrated in vacuo. The residue is chromatographed on silica gel eluting with ethyl acetate/hexane (⅝) to afford the title compound as a colorless oil (46 mg, 14%) which is characterized by $^1$HNMR, $^{13}$CNMR, $^{19}$FNMR, IR and mass spectral analyses.

What is claimed is:

1. A process for the preparation of a compound of formula I

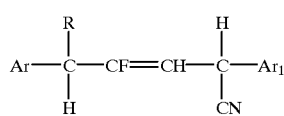

wherein

Ar is phenyl unsubstituted or substituted with any combination of from one to three halogen, $C_1$–$C_4$alkyl,
$C_1$–$C_4$haloalkyl, $C_1$–$C_4$alkoxy or $C_1$–$C_4$haloalkoxy groups, or 1- or 2-naphthyl unsubstituted or substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is hydrogen, $C_1$–$C_4$alkyl, $C_1$–$C_4$haloalkyl, $C_3$–$C_6$cycloalkyl or $C_3$–$C_6$halocycloalkyl; and $Ar_1$ is phenoxyphenyl unsubstituted or substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl unsubstituted or substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl unsubstituted or substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl unsubstituted or substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl unsubstituted or substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl unsubstituted or substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl unsubstituted or substituted with any combination of from one to five halogen, $C_1$–$C_4$ alkyl, $C_1$–$C_4$ haloalkyl, $C_1$–$C_4$ alkoxy or $C_1$ haloalkoxy groups, 1- or 2-naphthyl unsubstituted or substituted with any combination of from one to three halogen, $C_1$–$C_4$alkyl, $C_1$–$C_4$haloalkyl, $C_1$–$C_4$alkoxy or $C_1$–$C_4$haloalkoxy groups; or the optical isomers thereof; or
the cis and trans isomers thereof,
which process comprises the following steps:
a) reacting an intermediate of formula II

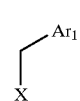

wherein $Ar_1$ is defined as above and X is chloro, bromo, iodo, tosyloxy, mesyloxy or the like with a cyanide delivering reagent in a first solvent to afford a cyano intermediate of formula III

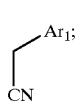

b) reacting said cyano intermediate III with an aldehyde of formula IV

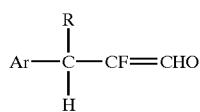

in the presence of a base in a second solvent to yield an anion which is acidified to afford a diene of formula V

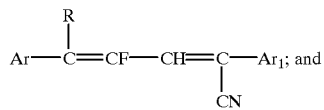

c) reacting said diene of formula V with magnesium in the presence of a third solvent to give the desired formula I product.

2. The process according to claim 1 wherein said cyanide delivering reagent is an alkali metal cyanide.

3. The process according to claim 2 wherein the alkali metal cyanide is sodium cyanide or potassium cyanide.

4. The process according to claim 1 wherein said first solvent is a polar aprotic solvent selected from the group consisting of dimethylsulfoxide, dimethylformamide and N-methylpyrrolidone.

5. The process according to claim 4 wherein the polar aprotic solvent is dimethylsulfoxide.

6. The process according to claim 1 wherein the said base is an alkali metal amide.

7. The process according to claim 6 wherein the alkali metal amide is lithium diisopropylamide.

8. The process according to claim 1 wherein said acid is a strong mineral acid.

9. The process according to claim 8 wherein said strong mineral acid is sulfuric acid or hydrochloric acid.

10. The process according to claim 1 wherein said third solvent is an alkanol.

11. The process according to claim 10 wherein the alkanol is methanol or ethanol.

* * * * *